(12) United States Patent
Omran et al.

(10) Patent No.: US 12,419,911 B1
(45) Date of Patent: Sep. 23, 2025

(54) METHOD OF TREATING CANCER USING A ZrO2@CaSiO3@g-C3N4 NANOCOMPOSITE MATERIAL

(71) Applicant: IMAM MOHAMMAD IBN SAUD ISLAMIC UNIVERSITY, Riyadh (SA)

(72) Inventors: Mohamed Khairy Abdel Fattah Omran, Riyadh (SA); Babiker Yagoub Elhadi Abdulkhair, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/214,778

(22) Filed: May 21, 2025

(51) Int. Cl.
*A61K 33/24* (2019.01)
*A61P 35/00* (2006.01)

(52) U.S. Cl.
CPC .............. *A61K 33/24* (2013.01); *A61P 35/00* (2018.01)

(58) Field of Classification Search
None
See application file for complete search history.

(56) References Cited

FOREIGN PATENT DOCUMENTS

| CN | 112939594 A | 6/2021 |
| CN | 119097641 A | 12/2024 |
| IN | 202311022975 A | 10/2024 |

OTHER PUBLICATIONS

Lili Feng, et al., "Multifunctional UCNPs@MnSiO3@g-C3N4 nanoplatform: improved ROS generation and reduced glutathione levels for highly efficient photodynamic therapy", Biomaterials Science, 2017, vol. 5, Issue 12, pp. 2456-2467, Abstract only, 2 pages.

Maqusood Ahamed, et al., "Biosynthesis, Characterization, and Augmented Anticancer Activity of ZrO2 doped ZnO/rGO Nanocomposite", Journal of Functional Biomaterials 2023, vol. 14, 38, Jan. 9, 2023, 13 pages.

Ashraf Elsayed et al., "Biosynthesis, Characterization, and Assessment of Zirconia Nanoparticles by Fusarium oxysporum species as Potential Novel Antimicrobial and Cytotoxic Agents", Egyptian Journal of Botany, vol. 62, No. 2, pp. 507-522, Mar. 29, 2022.

*Primary Examiner* — Brian J Davis
(74) *Attorney, Agent, or Firm* — Oblon, McClelland, Maier & Neustadt, L.L.P.

(57) ABSTRACT

A method of treating cancer cells includes exposing the cancer cells to a $ZrO_2/CaSiO_3/g-C_3N_4$ nanocomposite material. The $ZrO_2/CaSiO_3/g-C_3N_4$ nanocomposite material comprises spherical metal oxide nanoparticles comprising a $ZrO_2$ phase and a $CaSiO_3$ phase dispersed on a matrix of $g-C_3N_4$ nanosheets, wherein the spherical metal oxide nanoparticles have an average particle diameter in a range from 3 to 18 nm, and wherein the $ZrO_2/CaSiO_3/g-C_3N_4$ nanocomposite material has a percent inhibition for human breast carcinoma (MCF-7) cells greater than or equal to 80% inhibition in an in-vitro cellular viability assay.

20 Claims, 7 Drawing Sheets

METHOD OF TREATING CANCER USING A ZrO2@CaSiO3@g-C3N4 NANOCOMPOSITE MATERIAL

BACKGROUND

Technical Field

The present disclosure is directed to a nanocomposite and, more particularly, a method of treating cancer using a $ZrO_2/CaSiO_3@g-C_3N_4$ nanocomposite material.

Description of Related Art

The 'background' description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Worldwide, cancer remains a leading cause of death and disability due to a complex pathological process associated with a plurality of cancers. Conventional chemotherapy faces several challenges, including cytotoxicity, low therapeutic indices, low bioavailability, insolubility, high dose requirements, non-specific targeting, and the development of multiple drug resistance. Resistance to cancer treatment arises from various factors such as overexpression of drug efflux transporters, anoxic conditions, and abnormal apoptotic pathways. The aforementioned limitations necessitate the exploration of innovative approaches to improve cancer treatment efficacy and patient outcomes.

Nanomaterials (NMs) have emerged as promising anticancer agents to address the limitations of conventional chemotherapy. The optimization of NMs in terms of size, shape, and surface characteristics enhances targeting efficiency and prolongs circulation time, thereby increasing the targeting potential of anticancer cargos. NMs may enhance therapeutic efficacy through controlled release mechanisms by encapsulating or coupling therapeutic cargos with ligands, providing precise delivery to cancer sites. In cancer treatment, NMs are employed to target cancer cells, the tumor microenvironment, and the immune system through stimuli-responsive targeting or surface modification with targeting ligands such as transferrin, integrins, sugar, folic acid, and antibodies. The aforementioned functionalization may improve tissue targeting, recognition, and internalization, offering a more effective therapeutic approach. The biomedical applications of NMs are extensive, with their ability to transport ligands and therapeutic compounds or to target cancer cells and tissues through passive, active, or physical targeting methods. The above-described advancements aim to achieve stronger inhibitory therapeutic efficacies in the fight against cancer.

Research in this regard has been conducted, e.g., in Mandal, A., et al., *J. Drug Deliv. Therap.*, 2023, 13, 12, 201-223, and Algethami, F., et al., *Zeitschr. anorg. allg. Chem.*, 2021, 647, 19, 1921-1929, each of which are incorporated by reference herein. Despite certain improved therapeutic methods, the application of nanomaterials in cancer treatment faces several challenges and limitations. Key drawbacks include potential toxicity and long-term biocompatibility concerns, difficulties in large-scale production with consistent quality, and challenges in achieving efficient clearance from the body to avoid accumulation and adverse side effects. Additionally, regulatory and clinical translation hurdles pose significant challenges, requiring extensive preclinical and clinical validation to ensure safety and efficacy. The cost of developing and deploying nanomaterial-based therapies is yet another barrier to widespread clinical adoption.

Accordingly, one object of the present disclosure is to provide a method of inhibiting cancer cell viability, that may circumvent the above listed drawbacks and limitations of the methods known in the art.

SUMMARY

In an exemplary embodiment, a method of treating cancer cells is described. The method includes exposing the cancer cells to a $ZrO_2/CaSiO_3/g-C_3N_4$ nanocomposite material. The $ZrO_2/CaSiO_3/g-C_3N_4$ nanocomposite material comprises spherical metal oxide nanoparticles, including a $ZrO_2$ phase and a $CaSiO_3$ phase, dispersed on a matrix of $g-C_3N_4$ nanosheets. The spherical metal oxide nanoparticles have an average particle diameter in a range from 3 to 18 nm. The $ZrO_2/CaSiO_3/g-C_3N_4$ nanocomposite material has a percent inhibition for human Breast carcinoma (MCF-7) cells greater than or equal to 80% inhibition in an in-vitro cellular viability assay.

In some embodiments, the $ZrO_2/CaSiO_3/g-C_3N_4$ nanocomposite material has a percent inhibition for MCF-7 cells greater than or equal to 83% inhibition in an in-vitro cellular viability assay.

In some embodiments, the $ZrO_2/CaSiO_3/g-C_3N_4$ nanocomposite material has a percent inhibition for MCF-7 cells greater than or equal to 86% inhibition in an in-vitro cellular viability assay.

In some embodiments, the $ZrO_2/CaSiO_3/g-C_3N_4$ nanocomposite material has a percent inhibition for Human Hepatocellular Carcinoma (HepG-2) cells greater than or equal to 85% inhibition in an in-vitro cellular viability assay.

In some embodiments, the $ZrO_2/CaSiO_3/g-C_3N_4$ nanocomposite material has a percent inhibition for HepG-2 cells greater than or equal to 87% inhibition in an in-vitro cellular viability assay.

In some embodiments, the $ZrO_2/CaSiO_3/g-C_3N_4$ nanocomposite material has a percent inhibition for HepG-2 cells greater than or equal to 89% inhibition in an in-vitro cellular viability assay.

In some embodiments, the $ZrO_2/CaSiO_3/g-C_3N_4$ nanocomposite material has a 50% inhibitory concentration ($IC_{50}$) for MCF-7 cells less than or equal to 200 μg/ml.

In some embodiments, the $ZrO_2/CaSiO_3/g-C_3N_4$ nanocomposite material has an $IC_{50}$ for MCF-7 cells less than or equal to 180 μg/ml.

In some embodiments, the $ZrO_2/CaSiO_3/g-C_3N_4$ nanocomposite material has an $IC_{50}$ for MCF-7 cells less than or equal to 160 μg/ml.

In some embodiments, the $ZrO_2/CaSiO_3/g-C_3N_4$ nanocomposite material has an $IC_{50}$ for HepG-2 cells less than or equal to 160 μg/ml.

In some embodiments, the $ZrO_2/CaSiO_3/g-C_3N_4$ nanocomposite material has an $IC_{50}$ for HepG-2 cells less than or equal to 140 μg/ml.

In some embodiments, the $ZrO_2/CaSiO_3/g-C_3N_4$ nanocomposite material has an $IC_{50}$ for HepG-2 cells less than or equal to 120 μg/ml.

In some embodiments, the spherical metal oxide nanoparticles have an average particle diameter in a range from 5 to 12 nm.

In some embodiments, the spherical metal oxide nanoparticles have an average particle diameter of 8.5 nm.

In some embodiments, the $ZrO_2/CaSiO_3/g\text{-}C_3N_4$ nanocomposite material has a Brunauer-Emmett-Teller (BET) surface area greater than or equal to 55 $m^2 \cdot g^{-1}$.

In some embodiments, the $ZrO_2/CaSiO_3/g\text{-}C_3N_4$ nanocomposite material has a BET surface area greater than or equal to 60 $m^2 \cdot g^{-1}$.

In some embodiments, the $ZrO_2/CaSiO_3/g\text{-}C_3N_4$ nanocomposite material has a BET surface area greater than or equal to 65 $m^2 \cdot g^{-1}$.

In some embodiments, the $ZrO_2/CaSiO_3/g\text{-}C_3N_4$ nanocomposite material has a pore volume greater than or equal to 0.15 $cm^3 \cdot g^{-1}$.

In some embodiments, the $ZrO_2/CaSiO_3/g\text{-}C_3N_4$ nanocomposite material has a trimodal pore size distribution with average pore diameters maximized at 6.2, 9.53, and 17.2 nm.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
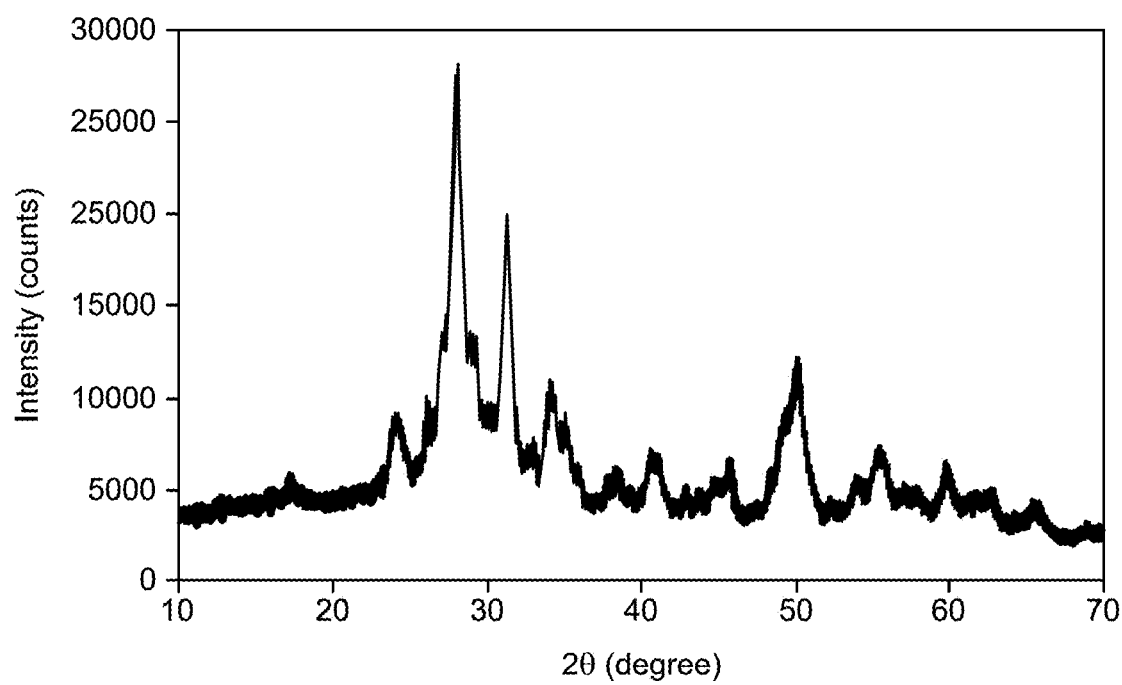
FIG. 1 shows X-ray diffractogram (XRD) of a $ZrO_2/CaSiO_3/g\text{-}C_3N_4$ nanocomposite, according to certain embodiments.
Figure 2A:
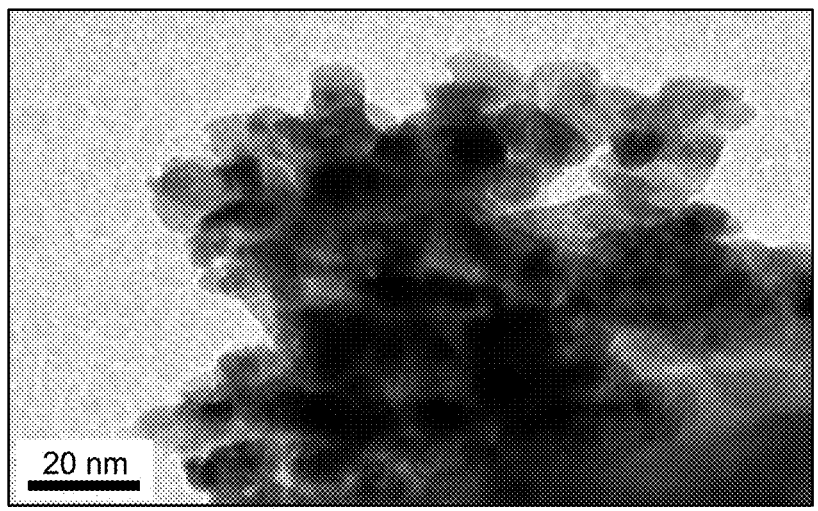
FIG. 2A is a transmission electron microscopy (TEM) image of the $ZrO_2/CaSiO_3/g\text{-}C_3N_4$ nanocomposite, at 20 nanometers (nm) magnification, according to certain embodiments.
Figure 2B:
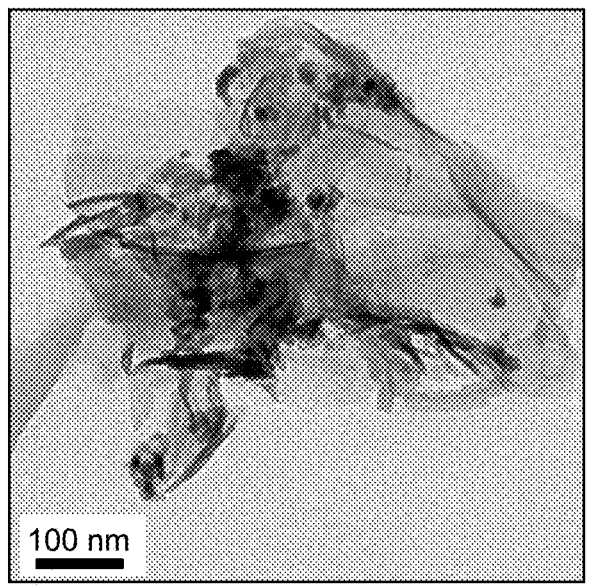
FIG. 2B is a TEM image of the $ZrO_2/CaSiO_3/g\text{-}C_3N_4$ nanocomposite at 100 nm magnification, according to certain embodiments.
Figure 2C:
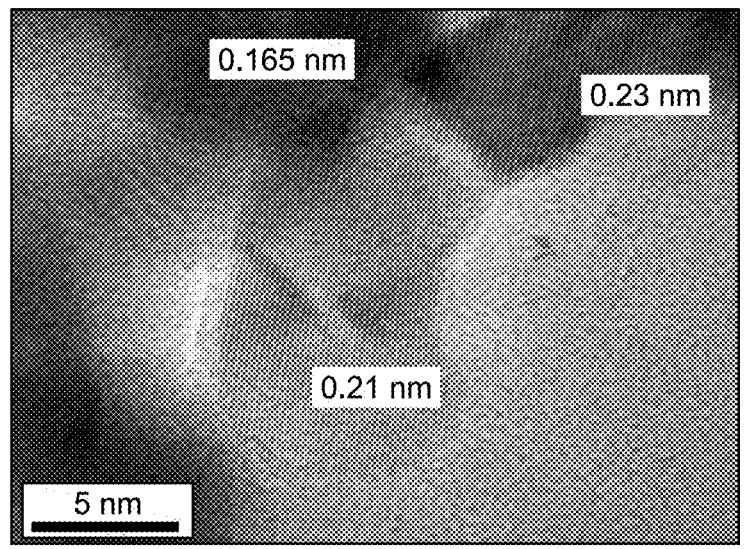
FIG. 2C is a high-resolution transmission electron microscope (HR-TEM) image of the $ZrO_2/CaSiO_3/g\text{-}C_3N_4$ nanocomposite, according to certain embodiments.
Figure 2D:
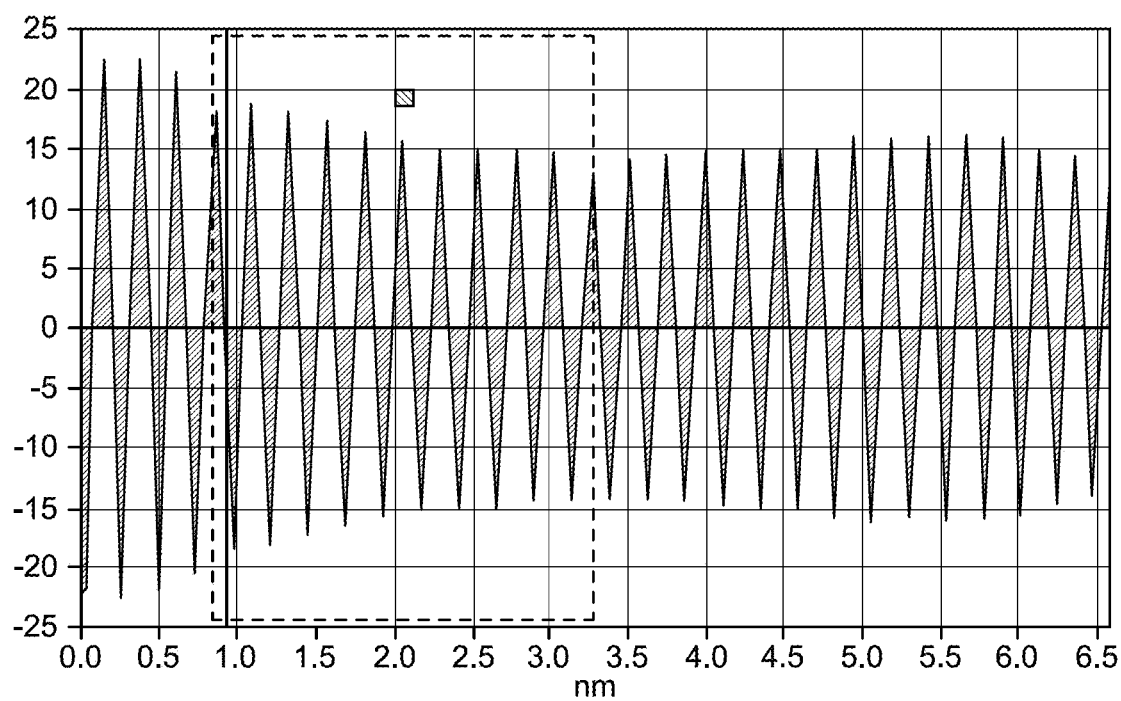
FIG. 2D is a fast Fourier transform (FFT) spectrum of the $ZrO_2/CaSiO_3/g\text{-}C_3N_4$ nanocomposite, according to certain embodiments.
Figure 2E:
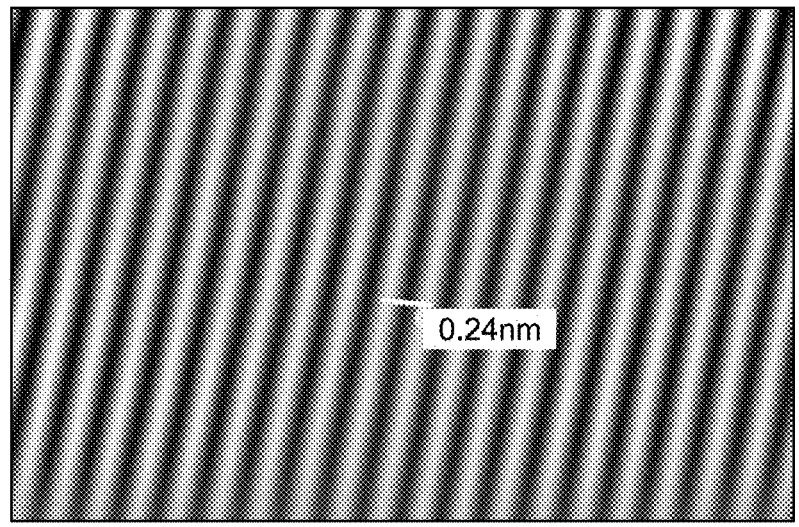
FIG. 2E is an inverse fast Fourier transform (IFFT) spectrum of the $ZrO_2/CaSiO_3/g\text{-}C_3N_4$ nanocomposite, according to certain embodiments.
Figure 2F:
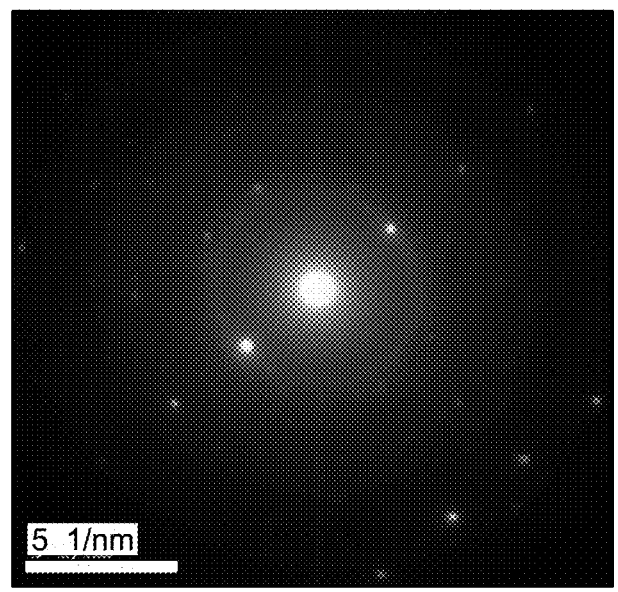
FIG. 2F is a selected area electron diffraction (SAED) pattern of the $ZrO_2/CaSiO_3/g\text{-}C_3N_4$ nanocomposite, according to certain embodiments.

When describing the present disclosure, the terms used are to be construed in accordance with the following definitions, unless a context dictates otherwise.

Embodiments of the present disclosure will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an, and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

A weight percent of a component, unless specifically stated to the contrary, is based on the total weight of the formulation or composition in which the component is included. For example, if a particular element or component in a composition or article is said to have 5 weight percentage (wt. %), it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the term 'porosity' refers to a measure of the void or vacant spaces within a material.

As used herein, the term 'pore diameter' refers to an average width or size of the pores (void spaces) within a material, typically measured in nm or angstroms (Å). It is a parameter in characterizing the texture and permeability of porous materials, influencing their adsorption, filtration, or catalytic properties. The pore diameter is often determined using methods such as nitrogen adsorption or mercury intrusion, which provide insights into the material's ability to absorb or interact with molecules of specific sizes.

As used herein, the term 'pore volume' refers to the total volume of void spaces (pores) within a material that is capable of being filled by a gas or liquid. It is typically expressed in cubic centimeters per gram ($cm^3/g$) and is an important parameter in characterizing the porous structure of materials, such as adsorbents or catalysts.

As used herein, the term 'cancer' refers to all types of cancer, neoplasm, or malignant tumors found in animals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the terms 'treat,' 'treatment,' and 'treating' in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. The subject is a mammalian subject. In one embodiment, the subject is a human. 'Treating' or 'treatment' of a disease may include preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in cancer stem cell population. Such terms may refer to a stabilization or reduction in the growth of cancer cells. Such terms may refer to stabilization or reduction in cancer stem cell population and a reduction in the cancer cell population. Such terms refer to a stabilization or reduction in the growth and or formation of a tumor. Such terms may refer to the eradication, removal, or control of primary, regional, or metastatic cancer (e.g., the minimization or delay of the spread of cancer). Such terms may refer to a reduction in mortality and/or an increase in the survival rate of a patient population. Such terms may refer to an increase in the response rate, the durability of response, or the number of patients who respond or are in remission. Such terms may refer to a decrease in the hospitalization rate of a patient population and/or a decrease in hospitalization length for a patient population.

As used herein, the term 'exposing' means any way of effectively delivering the nanocomposite material to cancer cells, including but not limited to oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Exposing is by any route, including parenteral and transmucosal (e.g., buccal, sublingual, palatal, gingival, nasal, vaginal, rectal, or transdermal). Parenteral exposure may include, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term 'cell viability' refers to the proportion of live, healthy cells in a population after being exposed to various conditions or treatments. It is commonly measured to assess the health and functionality of cells in laboratory studies, particularly when testing the effects of drugs, toxins, or other experimental variables. Viable cells can maintain their metabolism, growth, and division processes, while non-viable cells are damaged, dysfunctional, or dead. Cell viability is often assessed using assays that measure metabolic activity, membrane integrity, or other indicators of cellular health.

As used herein, the term 'nanoparticles (NPs)' refers to particles having a particle size of 1 nanometer (nm) to 1000 nm within the scope of the present disclosure.

As used herein, the term 'nanocomposite' is a material that is made by combining a matrix (often a polymer, metal, or ceramic) with NPs or nanomaterials to enhance its properties. The NPs are typically on the scale of nm (1 to 1000 nm), and their small size and high surface area can significantly improve the composite material's strength, thermal stability, electrical conductivity, optical properties, and other characteristics.

As used herein, percent inhibition refers to how much cancer cell growth has been reduced by a treatment compared to a control group. It is typically determined by comparing the number of cells in a treated group to a non-treated group, and is expressed as a percentage, where a higher percentage of inhibition indicates a greater reduction in cell growth. For example, a 50% inhibition of cancer cell growth means that 50% of the cancer cells proliferated in the treated group as compared to the control.

As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor or microorganism. $IC_{50}$ values are typically expressed as molar concentration.

As used herein, the term 'HepG-2 human hepatocellular carcinoma cells' refer to a type of cancer cell line derived from a liver tumor in a human patient.

As used herein, the term 'MCF-7 human breast carcinoma cells' refer to cell line derived from a breast cancer tumor.

Aspects of the present disclosure are directed to a method of treating cancer using a crystalline nanocomposite of a monoclinic $Bi_2O_3$ crystalline phase, a $CaSiO_3$ crystalline phase, and, a graphitic-$C_3N_4$ crystalline phase. When each component of the nanocomposite is used in appropriate ratios, the nanocomposite can effectively kills cancer cells.

According to one aspect of the present disclosure, a zirconium oxide ($ZrO_2$)/calcium silicate ($CaSiO_3$)/graphitic carbon nitride (g-$C_3N_4$) nanocomposite (referred to as a nanocomposite material) is used for treating cancer cells. The method includes exposing the cancer cells to the nanocomposite material in an amount sufficient to kill the cancer cells.

In one or more embodiments, the exposing is by way of oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Exposing is by any route, including parenteral and transmucosal (e.g., buccal, sublingual, palatal, gingival, nasal, vaginal, rectal, or transdermal).

The nanocomposite material has a percent inhibition for human breast carcinoma (MCF-7) cells greater than or equal to 60%, preferably greater than or equal to 80%, preferably greater than or equal to 83% inhibition, preferably greater than or equal to 86%, in an in-vitro cellular viability assay. In one embodiment, the nanocomposite material has a percent inhibition for MCF-7 cells of about 86.0% in an in-vitro cellular viability assay at a concentration of 500 µg/ml of the nanocomposite material. In some embodiments, the nanocomposite material has a 50% inhibitory concentration ($IC_{50}$) for MCF-7 cells less than or equal to 300 µg/ml, preferably less than or equal to 200 µg/ml, preferably less than or equal to 180 µg/ml, preferably less than or equal to 160 µg/ml. In one embodiment, the nanocomposite material has a $IC_{50}$ for MCF-7 cells of about 157.7 µg/ml.

The nanocomposite material has a percent inhibition for human hepatocellular carcinoma (HepG-2) cells greater than or equal to 65%, preferably greater than or equal to 85%, preferably greater than or equal to 87%, preferably greater than or equal to 89% than inhibition in an in-vitro cellular viability assay. In one embodiment, the nanocomposite material has a percent inhibition for HepG-2 cells of about 89.0% in an in-vitro cellular viability assay at a concentration of 500 µg/ml of the nanocomposite material. In some embodiments, the nanocomposite material has an $IC_{50}$ for HepG-2 cells less than or equal to 260 µg/ml, preferably less than or equal to 160 µg/ml, preferably less than or equal to 140 µg/ml, preferably less than or equal to 120 µg/ml. In one embodiment, the nanocomposite material has a $IC_{50}$ for HepG-2 cells of about 120.07 µg/ml.

A nanocomposite material including zirconium oxide/calcium silicate/graphitic carbon nitride ($ZrO_2$/$CaSiO_3$/g-$C_3N_4$) is described. The nanocomposite material includes spherical metal oxide nanoparticles consisting of a $ZrO_2$ phase and a $CaSiO_3$ phase dispersed on a matrix of g-$C_3N_4$ nanosheets. In one or more embodiments, the spherical metal oxide nanoparticles have an average particle diameter in a range from 1-30 nanometer (nm), preferably 3-18 nm, preferably 4-17 nm, preferably 4.5-16 nm, preferably 5-15, preferably 5-12 nm, preferably 5.5-11.5 nm, preferably 6-11 nm, preferably 6.5-10.5 nm, preferably 7-10 nm, preferably 7.5-9.5 nm and preferably 8-9 nm. In a preferred embodiment, the spherical metal oxide nanoparticles have an average particle diameter of 8.5 nm.

In one or more embodiments, the $ZrO_2$/$CaSiO_3$/g-$C_3N_4$ nanocomposite material has a $ZrO_2$ content in a range from 28 to 38 weight % (wt. %), a $CaSiO_3$ content in a range from 28 to 38 wt. %, and a g-$C_3N_4$ content in a range from 28 to 38 wt. %.

In some embodiments, the nanocomposite material is porous. Pores may be micropores, mesopores, macropores, and/or a combination thereof. The pores exist in the bulk material, not always in the molecular structure of the material. The term 'microporous' means that the crystalline nanocomposite has pores with an average pore width (i.e., diameter) of less than 2 nm. The term 'mesoporous' means the pores of the crystalline nanocomposite have an average pore width of 2-50 nm. The term 'macroporous' means the pores of the crystalline nanocomposite have an average pore width larger than 50 nm. Pore size may be determined by methods including, but not limited to, gas adsorption (e.g., $N_2$ adsorption), mercury intrusion porosimetry, and imaging techniques such as scanning electron microscopy (SEM) and X-ray computed tomography (XRCT).

In some embodiments, the nanocomposite material has a Brunauer-Emmett-Teller (BET) surface area greater than or equal to 40 square meters per gram ($m^2 \cdot g^{-1}$), preferably 55 $m^2 \cdot g^{-1}$, preferably greater than or equal to 56 $m^2 \cdot g^{-1}$, preferably greater than or equal to 57 $m^2 \cdot g^{-1}$, preferably greater than or equal to 58 $m^2 \cdot g^{-1}$, preferably greater than or equal to 59 $m^2 \cdot g^{-1}$, greater than or equal to 60 $m^2 \cdot g^1$, preferably greater than or equal to 61 $m^2 \cdot g^{-1}$, preferably greater than or equal to 62 $m^2 \cdot g^{-1}$, preferably greater than or equal to 63 $m^2 \cdot g^{-1}$, preferably greater than or equal to 64 $m^2 \cdot g^{-1}$ and greater than or equal to 65 $m^2 \cdot g^{-1}$. In a preferred embodiment, the surface area of the nanocomposite material is 66.5 $m^2 \, g^{-1}$. The BET surface area measurement is an analysis method for determining the specific surface area of a material. It relies on the physical adsorption of gas molecules on a solid surface. Specific surface area is a property of solids, the total surface area of a material is expressed per unit of mass, solid or bulk volume, or cross-sectional area. In some embodiments, pore diameter, pore volume, and BET surface area are measured by gas adsorption analysis, preferably $N_2$ adsorption analysis (e.g., $N_2$ adsorption isotherms).

In some embodiments, the nanocomposite material has a pore volume greater than or equal to 0.10 cubic centimeter per gram ($cm^3 \cdot g^{-1}$), preferably 0.15 $cm^3 \cdot g^{-1}$, preferably greater than or equal to 0.16 $cm^3 \cdot g^1$, preferably greater than or equal to 0.17 $cm^3 \cdot g^{-1}$, preferably greater than or equal to 0.18 $cm^3 \cdot g^{-1}$, preferably greater than or equal to 0.19 $cm^3 \cdot g^{-1}$, greater than or equal to 0.20 $cm^3 \cdot g^{-1}$, preferably greater than or equal to 0.21 $cm^3 \cdot g^{-1}$, preferably greater than or equal to 0.22 $cm^3 \cdot g^{-1}$, preferably greater than or equal to 0.23 $cm^3 \cdot g^{-1}$, preferably greater than or equal to 0.24 $cm^3 \cdot g^{-1}$ and greater than or equal to 0.25 $cm^3 \cdot g^{-1}$. In a preferred embodiment, the pore volume of the nanocomposite material is equal to 0.26 $cm^3 \cdot g^{-1}$.

In some embodiments, the nanocomposite material may have monomodal, bimodal, trimodal, polydisperse or uniform pore size distribution. In a preferred embodiment, the nanocomposite material has a trimodal pore size distribution with average pore diameters maximized at 6.2 nm, 9.53 nm and 17.2 nm.

EXAMPLES

The following examples demonstrate a method of treating cancer. The examples are provided solely for illustration and are not to be construed as limitations of the present disclosure, as many variations thereof are possible without departing from the spirit and scope of the present disclosure.

Example 1: Fabricating the $CaSiO_3$

Equal moles of calcium nitrate (0.5 g) and sodium metasilicate (0.37 g) were dispersed in 100 milliliters (mL) of ethanol:water (1:1) in a 150 mL glass beaker and sonicated for 15 minutes. The mixture was transferred to a 200 mL autoclave and then placed in an oven operated at 180° C. for 2 hours. The product was dispersed in 500 mL distilled water with an ultrasonic bath for 10 minutes, filtered via a Buchner system, rinsed with distilled water, and dried at 120° C. for 1 hour.

Example 2: Fabricating the $g-C_3N_4$

About 30 grams (g) of urea was placed in a 250 mL porcelain crucible, covered with its porcelain cover, then the crucible and cover were wrapped with three layers of aluminum foil to reduce the urea loss to sublimation. The crucible was heated via a furnace set at 600° C. for 45 minutes.

Example 3: Fabricating the $ZrO_2$

About 10 g zirconium oxychloride octahydrate and 10 g of xylose were placed in a 500 mL beaker. 100 mL distilled water was added to the mixture and heated till a clear solution was obtained. 10 mL of concentrated nitric acid was added to the mixture, which was then at 200° C. heated until the carbonization of xylose. The mixture was placed in an oven set at 200° C. for 3 hours, the black product was milled in a mortar, placed in a 150 mL porcelain dish, and calcined at 550° C. for 4 hours.

Example 4: Fabricating the $ZrO_2/CaSiO_3@g-C_3N_4$

An equal amount of $CaSiO_3$, $g-C_3N_4$, and $ZrO_2$ (0.5 grams each) was transferred to a mono wave-200 vial (G30), dispersed in 20 mL ethylene glycol monomethyl ether via an ultrasonic bath for 30 minutes. The vial was closed with its Teflon cover and placed in the Anton-Baar Monowave-200 operated at 180° C. and 5 bar pressure for one hour. The product was dispersed in 1 litre (L) distilled water with an ultrasonic bath for 30 minutes, filtered via a Buchner system, rinsed with distilled water, and dried at 150° C. for 2 hours.

Example 5: Anticancer Activity

Cell line Propagation: The cells were grown on RPMI-1640 medium supplemented with 10% inactivated fetal calf serum and 50 µg/ml gentamycin. The cells were maintained at 37° C. in a humidified atmosphere with 5% $CO_2$ and were sub-cultured two to three times a week.

Example 6: Cytotoxicity Evaluation Using Viability Assay

For antitumor assays, the tumor cell lines were suspended in a medium at concentration $5 \times 10^4$ cell/well in Corning 96-well tissue culture plates, then incubated for 24 hr. The tested compounds were then added into 96-well plates (three replicates) to achieve ten concentrations for each compound. Six vehicle controls with media were run for each 96-well plate as a control. After incubating for 24 h, the numbers of viable cells were determined by the MTT test. Briefly, the media was removed from the 96 well plates and replaced with 100 µl of fresh culture RPMI 1640 medium without phenol red, then 10 µl of the 12 mM MTT stock solution (5 mg of MTT in 1 mL of PBS) was added to each well including the untreated controls. The 96-well plates were incubated at 37° C. and 5% $CO_2$ for 4 hours. An 85 µl aliquot of the media was removed from the wells, and 50 µl of DMSO was added to each well, mixed thoroughly with the pipette, and then incubated at 37° C. for 10 min. Then after, the optical density was measured at 590 nm with the microplate reader (Sunrise, TECAN, Inc, USA) to determine the number of viable cells. The percentage of viability was calculated as $[(ODt/ODc)] \times 100\%$ where ODt is the mean optical density of wells treated with the tested sample and ODc is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

XRD was used to examine the crystallinity and phase identification of the $ZrO_2/CaSiO_3/g-C3N4$ catalyst; the findings are shown in FIG. 1. The powder's high crystalline nature is shown by its sharp peaks and high-intensity values. $ZrO_2$ is present as a major phase, and $CaSiO_3$ and $g-C_3N_4$ are minor phases, according to an analysis of the diffraction patterns using standard PDF cards. The 2Θ values of 23.9, 28.0, 31.3, 33.9, and 49.9° were used to index the $ZrO_2$ monoclinic phase. (011), (−11), (111), (002), and (220) planes of the monoclinic phase of $ZrO_2$ are ascribed to these diffractions, respectively (Reference code No. 01-074-0815). The 2Θ values of 20.4, 26.8, 28.9, 30.2, and 50.1° values were used to detect the $CaSiO_3$ phase (Reference code 01-072-2297). These diffractions originated from (21-1), (20-2), (202), (320), and (040), in that order. The $g-C_3N_4$ diffractions were recorded at 28.5 and 47.5° (Reference code No. 01-072-0497), indicating that $ZrO_2/CaSiO_3/g-C_3N_4$ was successfully fabricated since no further phases were found.

TEM images of $ZrO_2/CaSiO_3@g-C_3N_4$ nanocomposite were presented in FIG. 2. The TEM images showed a two-dimensional porous structure constructed with curled and wrinkled nanosheets and platelets of the $g-C_3N_4$ (FIG. 2A). The image also shows well-dispersed homogeneous spherical metal oxide nanoparticles with a size of about 8.5 nm on nanosheets of $g-C_3N_4$ (FIG. 2A and FIG. 2B). The corresponding SAED pattern reveals diffraction spots with interplanar spacing of 0.31 nm, 0.154 nm, and 0.13 nm due to ($CaSiO_3$: 202, $ZrO_2$: −111), ($ZrO_2$: −302, $C_3N_4$: 331, $CaSiO_3$: 54-1) and ($CaSiO_3$: 33-4, $ZrO_2$: 123), diffraction planes (FIG. 2F). The corresponding HRTEM of the composite shows a plane spacing of 0.23 nm related to the (002) of CN, where 0.165 nm and 0.21 nm are related respectively to the ($CaSiO_3$: 40-4, $ZrO_2$: −113) and ($CaSiO_3$: 512, $ZrO_2$: −112) planes are characterizing the heterostructure formation (FIG. 2C). The FFT and IFFT measurements show a d value of 0.24 nm given to $ZrO_2/CaSiO_3@g-C_3N_4$ nanocomposite, signifying the lattice spacing of ($C_3N_4$: 220), indicating the development of $g-C_3N_4$ structure (FIG. 2D and FIG. 2E, respectively).

Figure 3A:
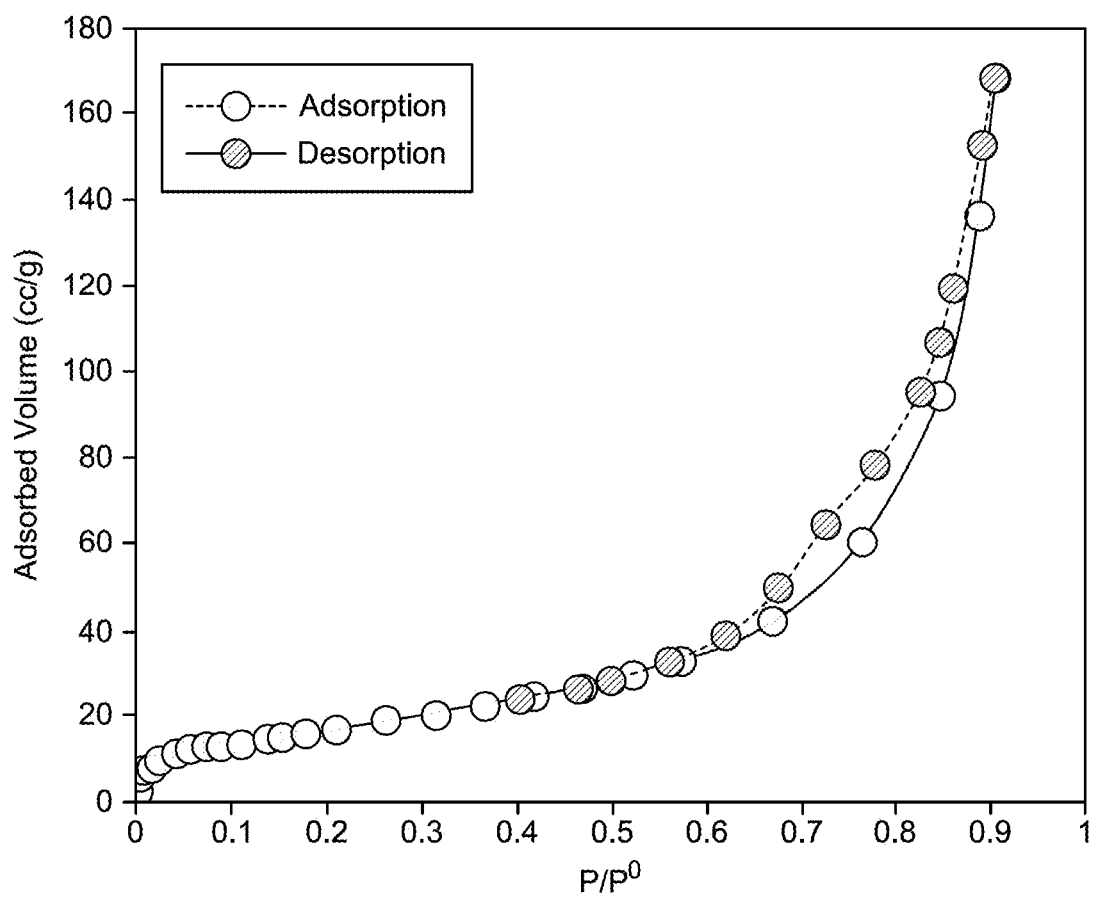
FIG. 3A is a graph depicting the nitrogen adsorption-desorption isotherm of the $ZrO_2/CaSiO_3/g\text{-}C_3N_4$ nanocomposite, according to certain embodiments.
Figure 3B:
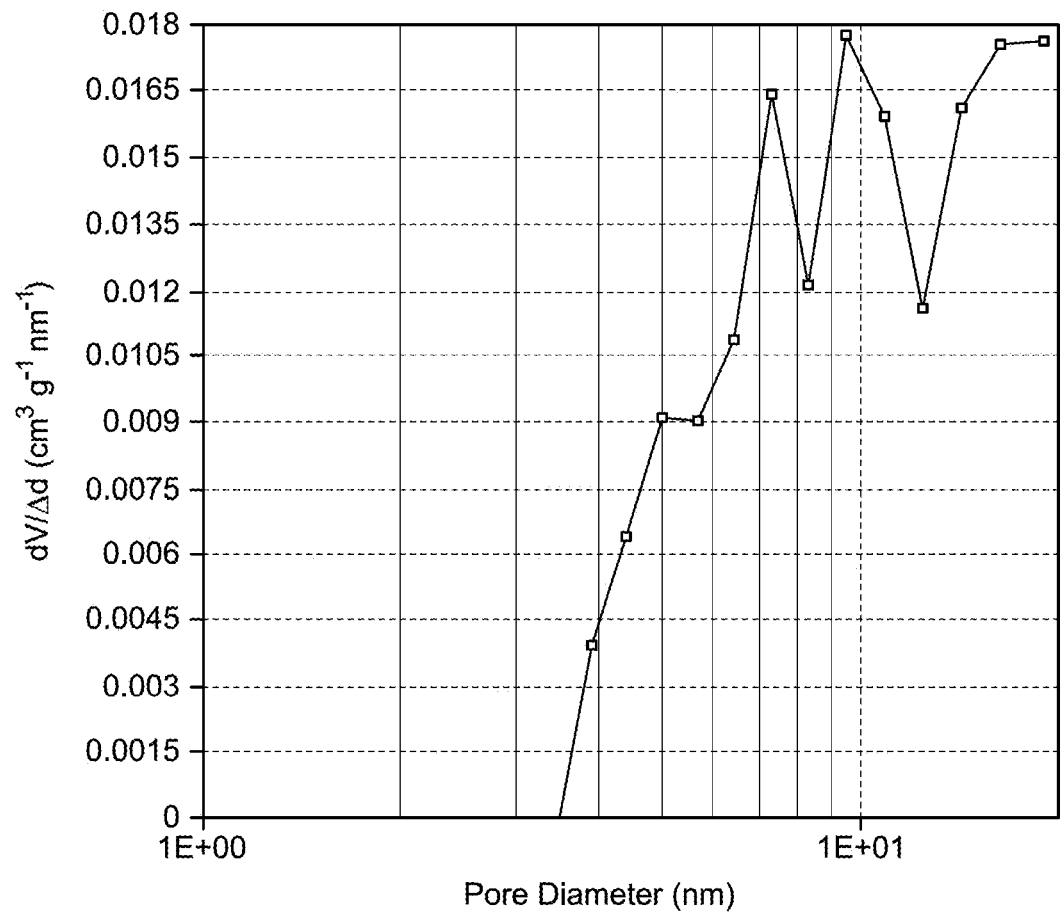
FIG. 3B is a graph depicting the pore size distribution of the $ZrO_2/CaSiO_3/g\text{-}C_3N_4$ nanocomposite, according to certain embodiments.

FIG. 3A displays the nitrogen adsorption-desorption isotherms of $ZrO_2/CaSiO_3$@g-$C_3N_4$ nanocomposite. The nitrogen sorption isotherm of the composite belongs to type IV with a narrow hysteresis loop, indicating the formation of mesoporous structures. However, shifting the loop to a relatively higher pressure (P/P0=0.58-1) indicates the presence of wide mesopores, which may result from the deposition of metal oxide particles in the wide pores of g-$C_3N_4$. Furthermore, the BET surface area of the $ZrO_2/CaSiO_3$@g-$C_3N_4$ sample was calculated to be 66.5 $m^2 g^{-1}$. The marked high specific surface area reflects the good dispersion of these metal oxide nanoparticles on g-$C_3N_4$. Moreover, the pore size distribution curves, plotted using the Barrett-Joyner-Halenda (BJH) method, for the $ZrO_2/CaSiO_3$@g-$C_3N_4$ sample exhibited trimodal distribution with average pore diameters maximized at 6.2, 9.53, and 17.2 nm and a pore volume of 0.26 $cm^3 g^{-1}$. All the isotherms belong to the category H3 type of pores, which do not exhibit limiting adsorption at high P/P°, and arise due to the aggregation of plate-like particles, giving rise to slit-shaped pores. This indicates that the assembly of $ZrO_2/CaSiO_3$@g-$C_3N_4$ composite provoked a mesoporous array (FIG. 3B).

Figure 4A:
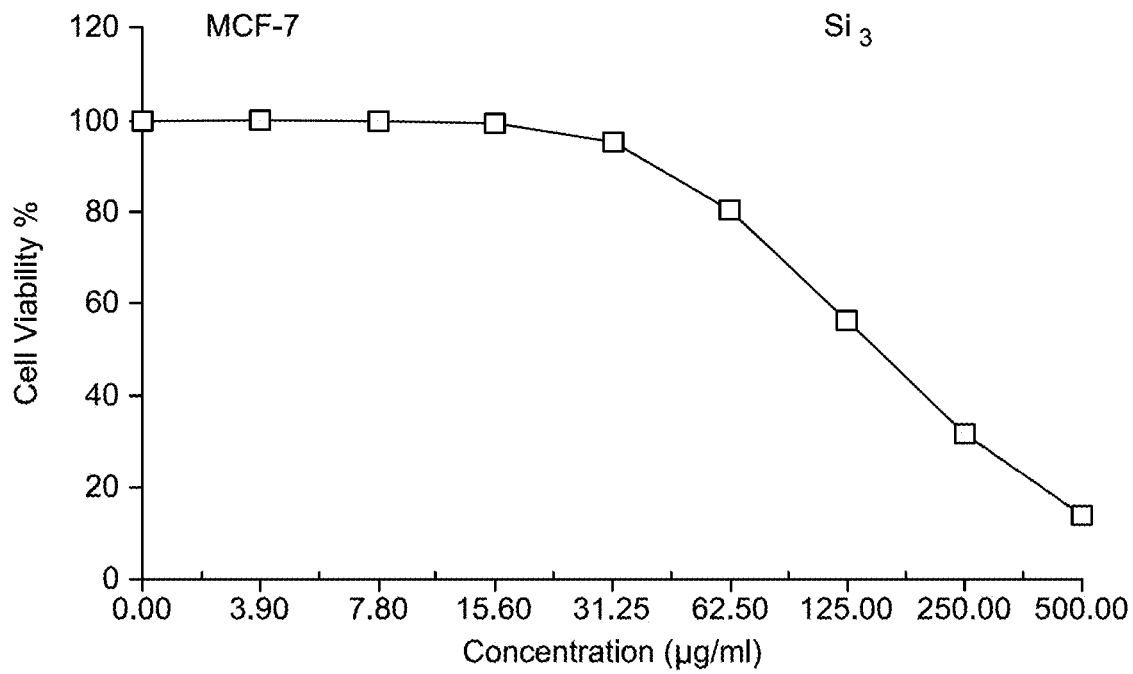
FIG. 4A is a graph depicting the inhibitory activity of the $ZrO_2/CaSiO_3/g\text{-}C_3N_4$ nanocomposite against MCF-7 cells, according to certain embodiments.
Figure 4B:
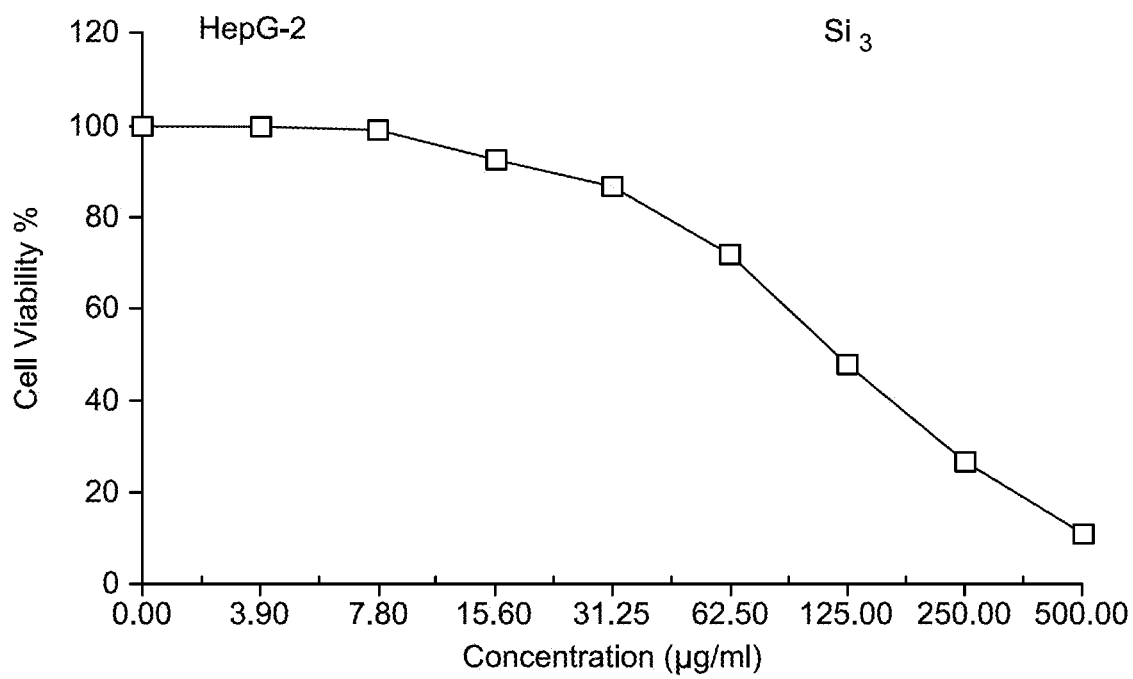
FIG. 4B is a graph depicting the inhibitory activity of the $ZrO_2/CaSiO_3/g\text{-}C_3N_4$ nanocomposite against HepG-2 cells, according to certain embodiments.

An in-vitro investigation was conducted for the $ZrO_2/CaSiO_3$@g-$C_3N_4$ against the human hepatocellular carcinoma (HepG-2) and human breast carcinoma cell lines (MCF-7). A concentration range of 3.0 to 500 µg/ml $ZrO_2/CaSiO_3$@g-$C_3N_4$ and the obtained results against the MCF-7 cell line is illustrated in FIG. 4A. The MCF-7 cell's viability started declining with only a 15.6 µg/ml $ZrO_2/CaSiO_3$@g-$C_3N_4$ dose, the $IC_{50}$ was 157.7 µg/ml, and the maximum dose (500 µg/ml) showed a 86.0% inhibition of the MCF-7. Furthermore, the exact concentration range of 3.0 to 500 µg/ml $ZrO_2/CaSiO_3$@g-$C_3N_4$ was applied against the HepG-2 cell line, and the obtained results are illustrated in FIG. 4B. The HepG-2 cell's viability started declining with only a 7.8 µg/ml $ZrO_2/CaSiO_3$@g-$C_3N_4$ dose. The $IC_{50}$ was 120.07 µg/ml, and the maximum dose (500 µg/ml) showed an 89% inhibition of the HepG-2.

Numerous modifications and variations of the present disclosure are possible in light of the above teachings. It is, therefore, to be understood that within the scope of the appended claims, the disclosure may be practiced otherwise than as specifically described herein.

The invention claimed is:

1. A method of treating cancer cells, comprising:
exposing the cancer cells to a $ZrO_2/CaSiO_3$/g-$C_3N_4$ nanocomposite material,
wherein the $ZrO_2/CaSiO_3$/g-$C_3N_4$ nanocomposite material comprises spherical metal oxide nanoparticles comprising a $ZrO_2$ phase and a $CaSiO_3$ phase dispersed on a matrix of g-$C_3N_4$ nanosheets,
wherein the spherical metal oxide nanoparticles have an average particle diameter in a range from 3 to 18 nm, and
wherein the $ZrO_2/CaSiO_3$/g-$C_3N_4$ nanocomposite material has a percent inhibition for human Breast carcinoma (MCF-7) cells greater than or equal to 80% inhibition in an in-vitro cellular viability assay.

2. The method of claim 1, wherein the $ZrO_2/CaSiO_3$/g-$C_3N_4$ nanocomposite material has a percent inhibition for MCF-7 cells greater than or equal to 83% inhibition in an in-vitro cellular viability assay.

3. The method of claim 2, wherein the $ZrO_2/CaSiO_3$/g-$C_3N_4$ nanocomposite material has a percent inhibition for MCF-7 cells greater than or equal to 86% inhibition in an in-vitro cellular viability assay.

4. The method of claim 1, wherein the $ZrO_2/CaSiO_3$/g-$C_3N_4$ nanocomposite material has a percent inhibition for Human Hepatocellular Carcinoma (HepG-2) cells greater than or equal to 85% inhibition in an in-vitro cellular viability assay.

5. The method of claim 4, wherein the $ZrO_2/CaSiO_3$/g-$C_3N_4$ nanocomposite material has a percent inhibition for HepG-2 cells greater than or equal to 87% inhibition in an in-vitro cellular viability assay.

6. The method of claim 5, wherein the $ZrO_2/CaSiO_3$/g-$C_3N_4$ nanocomposite material has a percent inhibition for HepG-2 cells greater than or equal to 89% inhibition in an in-vitro cellular viability assay.

7. The method of claim 1, wherein the $ZrO_2/CaSiO_3$/g-$C_3N_4$ nanocomposite material has a 50% inhibitory concentration ($IC_{50}$) for MCF-7 cells less than or equal to 200 µg/ml.

8. The method of claim 7, wherein the $ZrO_2/CaSiO_3$/g-$C_3N_4$ nanocomposite material has an $IC_{50}$ for MCF-7 cells less than or equal to 180 µg/ml.

9. The method of claim 8, wherein the $ZrO_2/CaSiO_3$/g-$C_3N_4$ nanocomposite material has an $IC_{50}$ for MCF-7 cells less than or equal to 160 µg/ml.

10. The method of claim 1, wherein the $ZrO_2/CaSiO_3$/g-$C_3N_4$ nanocomposite material has an $IC_{50}$ for HepG-2 cells less than or equal to 160 µg/ml.

11. The method of claim 10, wherein the $ZrO_2/CaSiO_3$/g-$C_3N_4$ nanocomposite material has an $IC_{50}$ for HepG-2 cells less than or equal to 140 µg/ml.

12. The method of claim 11, wherein the $ZrO_2/CaSiO_3$/g-$C_3N_4$ nanocomposite material has an $IC_{50}$ for HepG-2 cells less than or equal to 120 µg/ml.

13. The method of claim 1, wherein the spherical metal oxide nanoparticles have an average particle diameter in a range from 5 to 12 nm.

14. The method of claim 13, wherein the spherical metal oxide nanoparticles have an average particle diameter of 8.5 nm.

15. The method of claim 1, wherein the $ZrO_2/CaSiO_3$/g-$C_3N_4$ nanocomposite material has a BET surface area greater than or equal to 55 $m^2 \cdot g^{-1}$.

16. The method of claim 15, wherein the $ZrO_2/CaSiO_3$/g-$C_3N_4$ nanocomposite material has a BET surface area greater than or equal to 60 $m^2 \cdot g^{-1}$.

17. The method of claim 16, wherein the $ZrO_2/CaSiO_3$/g-$C_3N_4$ nanocomposite material has a BET surface area greater than or equal to 65 $m^2 \cdot g^{-1}$.

18. The method of claim 1, wherein the $ZrO_2/CaSiO_3$/g-$C_3N_4$ nanocomposite material has a pore volume greater than or equal to 0.15 $cm^3 \cdot g^{-1}$.

19. The method of claim 18, wherein the $ZrO_2/CaSiO_3$/g-$C_3N_4$ nanocomposite material has a pore volume greater than or equal to 0.25 $cm^3 \cdot g^{-1}$.

20. The method of claim 1, wherein the $ZrO_2/CaSiO_3$/g-$C_3N_4$ nanocomposite material has a trimodal pore size distribution with average pore diameters maximized at 6.2, 9.53, and 17.2 nm.

* * * * *